United States Patent [19]

Acken

[11] Patent Number: 5,324,311
[45] Date of Patent: Jun. 28, 1994

[54] COAXIAL BIPOLAR CONNECTOR ASSEMBLY FOR IMPLANTABLE MEDICAL DEVICE

[75] Inventor: Alfred D. Acken, Sylmar, Calif.

[73] Assignee: Siemens Pacesetter, Inc., Sylmar, Calif.

[21] Appl. No.: 940,567

[22] Filed: Sep. 4, 1992

[51] Int. Cl.$^5$ ............................................. A61N 1/00
[52] U.S. Cl. ....................................... 607/37; 439/675; 607/116
[58] Field of Search .................... 128/419 P, 786; 439/578, 582, 675

[56]  References Cited
U.S. PATENT DOCUMENTS

| 3,302,159 | 1/1967 | Schumacher | 439/675 |
| 4,764,132 | 8/1988 | Stutz, Jr. | 439/810 |
| 4,782,836 | 11/1988 | Alt | 128/419 P G |
| 4,848,346 | 7/1989 | Crawford | 128/419 P |
| 4,934,366 | 6/1990 | Truex et al. | 128/419 P |
| 4,963,105 | 10/1990 | Lewis et al. | 439/578 |
| 4,971,057 | 11/1990 | Alt | 128/419 P |
| 5,012,807 | 5/1991 | Stutz, Jr. | 128/419 P |
| 5,074,809 | 12/1991 | Rousseau | 439/675 |
| 5,076,270 | 12/1991 | Stutz, Jr. | 128/419 P |
| 5,082,453 | 1/1992 | Stutz, Jr. | 439/265 |

Primary Examiner—William E. Kamm
Assistant Examiner—Scott M. Getzow
Attorney, Agent, or Firm—Malcolm J. Romano

[57] ABSTRACT

A compact connector assembly for an implantable medical device includes a receptacle for receiving the proximal end of a coaxial bipolar lead having a distal end attachable to a desired tissue location. The receptacle includes an open end for receiving the proximal end of the lead and a closed end carrying a conductive pin. The pin has a portion inside the receptacle projecting toward the open end thereof and adapted to make electrical contact with one of the lead conductor terminals. The proximal end of the lead has a conductive socket for receiving the projecting portion of the pin inside the receptacle. An adapter terminal may be used to convert the proximal end of the lead to the industry VS-1 standard.

18 Claims, 2 Drawing Sheets

COAXIAL BIPOLAR CONNECTOR ASSEMBLY FOR IMPLANTABLE MEDICAL DEVICE

FIELD OF THE INVENTION

The present invention relates generally to implantable medical devices such as cardiac pacemakers and particularly to a connector assembly for such devices including a receptacle and a lead for providing a reliable electrical connection between a desired tissue location and the electronic circuits of the implantable medical device.

BACKGROUND OF THE INVENTION

Although it will become evident to those skilled in the art that the present invention is applicable to a variety of implantable medical devices utilizing pulse generators to stimulate selected body tissue, the invention and its background will be described in terms of a specific example of such devices, namely, cardiac pacemakers for providing precisely controlled stimulation pulses to the heart.

Present day cardiac pacemakers are typically designed to be implanted in a "pocket" of fatty tissue near the patient's upper breast or lower abdomen. Accordingly, the electronic circuits within the pacemaker are hermetically sealed within a housing made of a material compatible with body tissue. Electrical connection is made with the pacemaker electronic circuits via feedthrough terminals that pass through the hermetically sealed housing. The feedthrough terminals are electrically connected to a connector receptacle in the pacemaker housing for receiving the proximal end of a pacing lead. The lead has a distal end having electrodes attached to the desired tissue location. For cardiac pacing, such a lead is typically inserted through one of the main veins of the patient, for example, the superior vena cava so that the distal end of the lead is directed inside the heart.

Good electrical contact must be maintained between the proximal end of the pacing lead and the pacing lead receptacle on the pacemaker. Further, the connection must be secure so that it does not come apart during use yet it must be detachable in the event the pacemaker or lead needs to be replaced. Moreover, the connection must at all times remain insulated and sealed from body fluids; such fluids are conductive and could cause an electrical short if permitted to infiltrate the connector assembly.

Multiconductor pacing leads such as coaxial bipolar leads include a pin electrode projecting from the proximal tip or extremity of the lead and one or more proximal ring electrodes. The pin and ring electrodes are designed to make secure electrical contact with mating terminals carried by the pacemaker lead receptacle. Recently, there has been an effort to standardize this interface between the pacing lead and pacemaker. See, for example, Calfee et al., "A Voluntary Standard For 3.2 mm Unipolar and Bipolar Pacemaker Leads and Connectors,"*PACE*, Vol. 9, pp. 1181-85 (November-December 1986). The standard described therein, now referred to by the designation VS-1 (Voluntary Standard - 1), has been adopted by most pacemaker manufacturers worldwide. Among other things, the VS-1 standard defines and specifies the dimensions of the pacing lead and the pacemaker receptacle into which the proximal end of the pacing lead is inserted. Examples of VS-1 connectors are shown in U.S. Pat. Nos. 5,076,270; 5,012,807; 4,848,346; and 4,934,366.

The very nature of an implantable device makes it desirable, of course, to reduce as much as possible the size of the housing of such a device. The VS-1 standard connector receptacle/pacing lead dimensions are factors which contribute to determining the size of the housing of the implantable medical device. It has now become evident that these standard dimensions place constraints on the ability to reduce the size of the housing. Accordingly, it would be desirable to have a connector assembly that removes the constraints imposed by the VS-1 standard connector assembly dimensions so as to permit the design of more compact implantable medical devices. At the same time, it would also be desirable for the pacing lead comprising part of such an assembly to be adaptable for use with pacemakers having pacing lead receptacles complying with the VS-1 standard.

SUMMARY OF THE INVENTION

In accordance with one aspect of the present invention, there is provided for use in an implantable medical device connector assembly a novel receptacle adapted to receive the proximal end of a coaxial, bipolar lead. The receptacle is adapted to connect the conductor terminals of the lead to the electronic circuits of the implantable medical device. The receptacle comprises a side wall, an open end for receiving the proximal end of the lead, and a closed end. The closed end of the receptacle carries an electrically conductive pin, a portion of which is disposed inside the receptacle and projects toward the open end thereof and which is adapted to make electrical contact with one of the lead conductor terminals. The end of the pin opposite the interior portion thereof is adapted for connection to the electronic circuits of the implantable medical device. The receptacle includes in the side wall thereof a terminal for coupling the other of the lead conductor terminals to the electronic circuits of the implantable medical device.

Pursuant to another aspect of the invention, there is provided a coaxial, bipolar lead having a novel proximal end which is adapted to mate with the aforedescribed receptacle. A conductive socket at the proximal end of the lead has a first portion connected to the inner conductor of the coaxial lead and a second portion proximate the tip of the lead adapted to receive the inwardly projecting portion of the conductive pin in the receptacle. By eliminating the pin projecting from the tip of a standard VS-1 connector along with the associated pin-receiving block on the connector cavity of the standard connector assembly, the overall length of the connector assembly is substantially reduced thereby making possible the design of more compact implantable medical devices.

According to yet another aspect of the present invention, the lead of the invention may be made to be compatible with an existing VS-1 connector assembly by means of an adapter terminal having at one end a projecting tip electrode conforming to VS-1 standard dimensions and at the other end a pin adapted to be received by the conductive socket at the proximal end of the lead.

BRIEF DESCRIPTION OF THE DRAWINGS

Further objects, advantages and features of the invention will become apparent from the detailed description of the preferred embodiment when read in conjunction with the accompanying drawings in which.

DESCRIPTION OF THE PREFERRED EMBODIMENT

Figure 1:
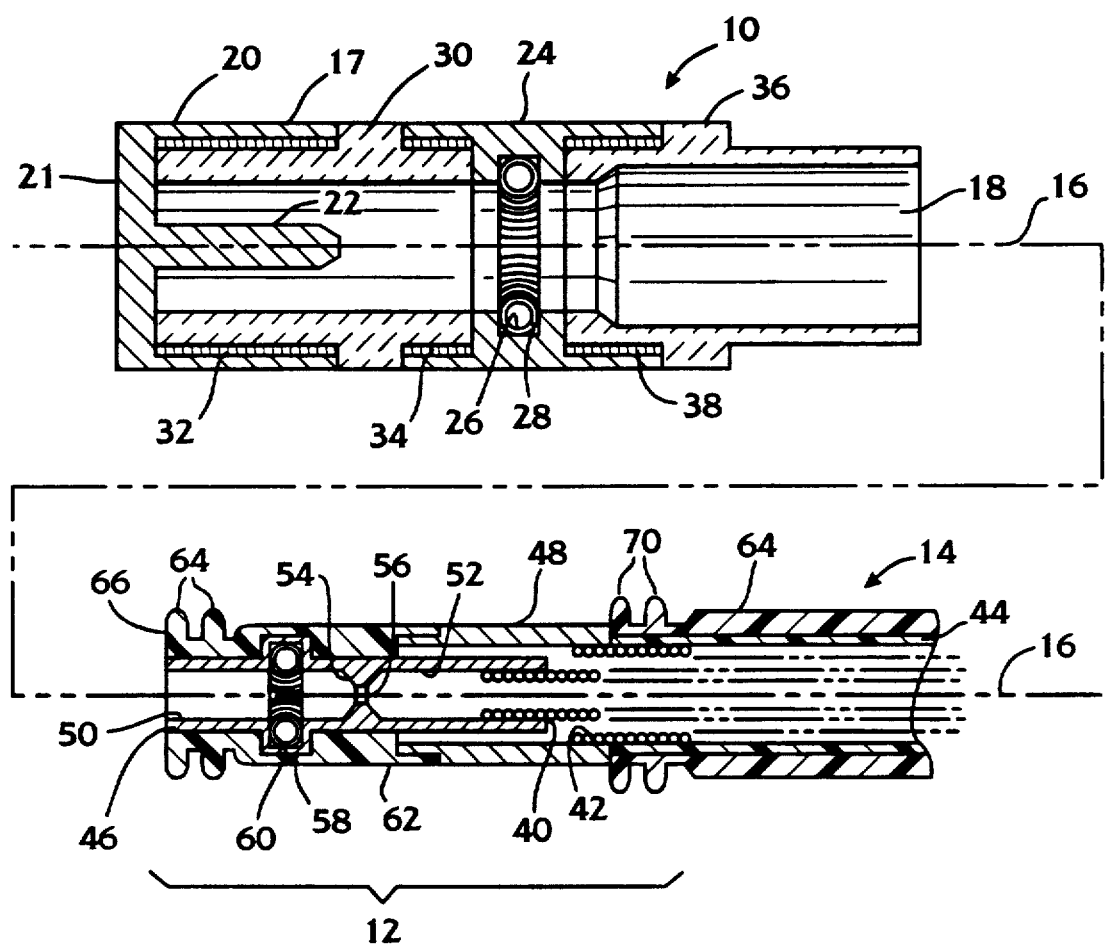
FIG. 1 is a longitudinal cross-section of a pacemaker connector assembly including a receptacle and the corresponding proximal end of a coaxial, bipolar lead, in accordance with the invention.

Referring to FIG. 1, there is shown a connector assembly including a connector cavity or receptacle 10 forming part of a cardiac pacemaker and the proximal end 12 of a pacing lead 14 adapted to be releasably received by the receptacle 10 for coupling the electronic pulse circuits of the pacemaker to the heart to be stimulated thereby.

The receptacle 10 is basically a tubular structure symmetrical about a longitudinal central axis 16 and having a cylindrical a side wall 17. The receptacle has an open end 18 and an opposite end closed by a cup shaped conductive terminal 20 having an end wall 21. The terminal 20 includes a conductive pin 22 extending inwardly along the central axis 16 toward the open end 18 of the receptacle. The terminal 20 comprises one of a pair of receptacle terminals adapted to be coupled to the electronic circuits of the cardiac pacemaker. The other terminal, identified by the reference numeral 24, is in the form of a ring having a generally T-shaped cross-sectional configuration as best seen in the upper portion of FIG. 1. The inner surface of the central portion of the receptacle ring terminal 24 has an annular groove 26 within which is retained a conductive garter spring contact 28. Interposed between the terminals 20 and 24 and isolating them electrically is a ceramic insulator tube 30 hermetically bonded to the terminals 20 and 24 by glass seals 32 and 34, respectively. A second ceramic insulator tube 36, defining the open end 18 and also hermetically bonded to the ring electrode 24 by a glass seal 38, extends to the right from the ring terminal 24 as seen in FIG. 1 and completes the structure of the receptacle 10. Although ceramic material is preferred for the insulating tubes 30 and 36, any suitable nonconductive material, such as an epoxy or polymer substance, could be used to perform this insulating function provided suitable hermetic bonds are made between the insulators and the terminals 20 and 24. In applications where hermeticity is not required, that is, when the connector elements are cast into an epoxy connector top outside of the hermetic electronics enclosure such as shown in U.S. Pat. No. 5,012,807, the insulative function may be performed by plastic materials that do not require hermetic bonding.

The pacing lead 14 is a two conductor lead commonly known in the art as a coaxial bipolar lead. Thus, the lead 14 includes an inner helically wound conductor 40 surrounded by an outer helically wound conductor 42. As is known, these conductors (only portions of which are shown in FIG. 1) are separated by an insulating layer (not shown) and the outer conductor is covered by an insulating sleeve a portion 44 of which is shown in the lower part of FIG. 1. The proximal lead end 12 includes an inner lead conductor terminal in the form of a conductive, longitudinally extending, tubular pin socket 46 of stainless steel or the like disposed along the central axis 16. The proximal lead end 12 also has an outer lead conductor terminal in the form of a conductive ring 48 also of stainless steel or similar material. The pin socket 46 has two sections: an outer section 50 adapted to receive the pin 22 and an inner section 52 for receiving the inner lead conductor 40. The socket sections 50 and 52 are separated by a transverse wall 54 having a central aperture 56 through which a stylet guide wire may be temporarily inserted during the implantation procedure. The wall of pin receiving section 50 includes an annular recess 58 retaining a garter spring contact 60 which assures a secure, low resistance connection between the pin 22 and the socket 46 when the proximal end 12 of the pacing lead is in place within the receptacle 10. A like, secure connection is provided by the garter spring contact 28 between the ring terminals 24 and 48.

Surrounding an outer portion of the socket 46 is a first elastomeric sealing sleeve 62 having a set of sealing rings 64 adjacent the tip 66 of the pacing lead. Similarly, a second elastomeric sealing sleeve 64 having a set of sealing rings 70 is disposed adjacent the ring terminal 48 to the right thereof as seen in FIG. 1. As is well known, the sealing rings 64 and 70 cooperate with the interior wall of the receptacle when the proximal end 12 of the pacing lead is inserted into the receptacle 10 to prevent body fluids from penetrating the receptacle and possibly causing an electrical malfunction. The sleeves 62 and 68 may be made of any resilient, moldable material such as silicone compatible with body tissue.

Figure 2:
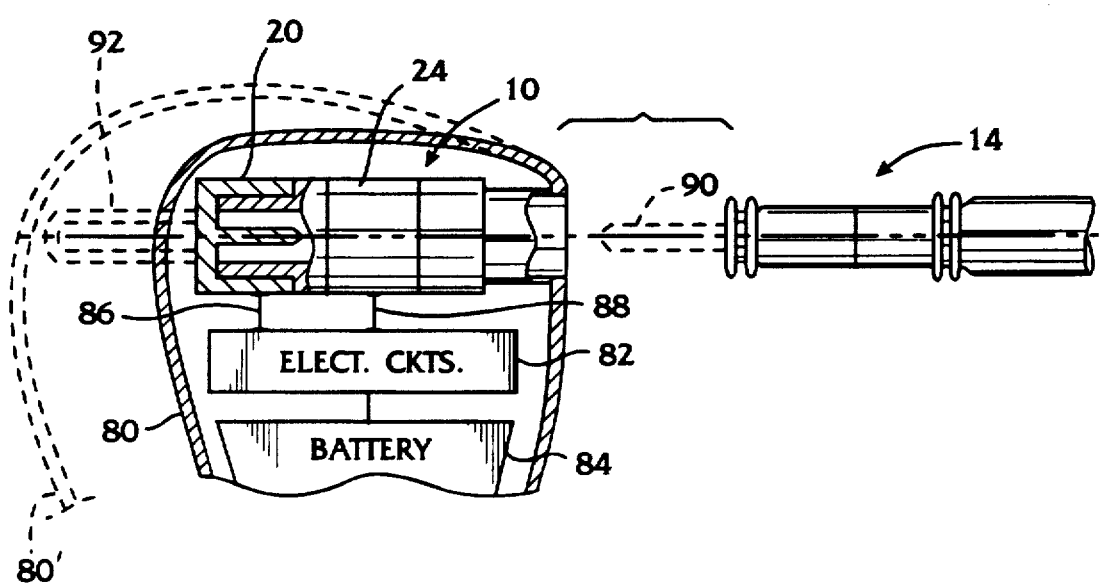
FIG. 2 is a side elevation view, partly in section, comparing the length of a connector assembly according to the present invention with that of a typical connector assembly of the prior art complying with the VS-1 standard.

FIG. 2 shows the receptacle 10 of the present invention incorporated into a cardiac pacemaker having a housing 80, electronic circuits 82 and a power supply in the form of a battery 84. Conductors 86 and 88 connect the electronic circuits 82 to the receptacle pin terminal 20 and ring terminal 24, respectively. FIG. 2 also compares the envelope of the housing 80 with that of a housing 80' of a pacemaker utilizing a standard VS-1 connector system. Such a standard system, shown in phantom in FIG. 2 for comparison purposes, includes a pin 90 projecting from the tip of the pacing lead along with a mating socket 92 for receiving the pin. It will thus be seen that the receptacle 10 of the present invention is substantially shorter than that of the VS-1 system making possible a substantial reduction in the overall width of the pacemaker housing.

Figure 3:
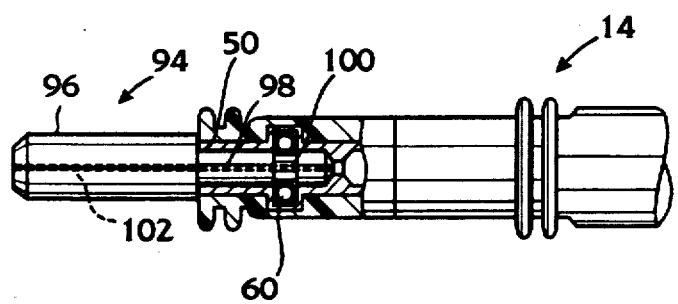
FIG. 3 is a side elevation view, partly in cross-section, of the proximal end of a pacing lead in accordance with the present invention shown in combination with a tip electrode adapter for converting the pacing lead to conform to the VS-1 standard.

The pacing lead 14 of the present invention can be adapted to be compatible with an existing VS-1 pacemaker connector assembly. In this regard, FIG. 3 shows an adapter terminal 94 having a projecting tip electrode 96 conforming to VS-1 standard dimensions and a pin 98 received by the pin socket 50 in the end of the pacing lead. For good electrical contact, the pin 98 may be provided with an annular groove 100 for mating with the garter spring contact 60. The adapter terminal 94 may also include an axially extending passageway 102 through which a stylet guide wire may be temporarily inserted.

The preceding describes the best mode presently contemplated of carrying out the invention. This description is not to be taken in a limiting sense but is made for the purpose of describing the general principles of the invention. Accordingly, the scope of the invention should be determined with reference to the appended claims and all equivalent structures are intended to be covered thereby.

What is claimed is:

1. In a connector assembly for an implantable medical device having electronic circuits, said connector assembly including a receptacle adapted to receive the proximal end of a bipolar lead having a pair of coaxial conductors and associated terminals, the receptacle being adapted to connect the conductors of the lead to the electronic circuits of said implantable medical device, the receptacle comprising:

a side wall, an open end for receiving the proximal end of the lead, and a closed, electrically conductive end wall, said closed end wall carrying an electrically conductive pin and being electrically connected thereto, a portion of said pin being disposed inside said receptacle ad projecting toward said open end thereof, the pin including an end opposite the inside portion for connection tot he circuits of said implantable medical device, the inside portion of the pin being adapted to make electrical contact with one of the lead terminals, said receptacle including in the side wall thereof a terminal for coupling the outer of said lead terminals to said circuits of said implantable medical device, said receptacle further comprising an elongated tubular structure having a central longitudinal axis, said electrically conductive pin and closed end wall being centered on said longitudinal axis.

2. A receptacle, as defined in claim 1, in which the terminal in the side wall of the receptacle comprises a conductive ring including yieldable contact means adapted to engage said other of said lead terminals.

3. A receptacle, as defined in claim 2, in which the pin is integral with said closed end wall.

4. A receptacle, as defined in claim 3, in which said receptacle includes an insulating tubular section interposed between the conductive ring and the conductive end wall.

5. A bipolar lead for providing an electrically conductive path between an implantable medical device and a desired tissue location, said implantable medical device having electronic circuits, the lead being adapted to be received by a receptacle on the implantable medical device and including a pair of coaxial conductors including an inner conductor and an outer conductor, said conductors being insulated from each other, the lead having a distal end for connection to said desired tissue location, a proximal end for connection to the electronic circuits of said implantable medical device and a tip, the lead including:

a conductive socket mounted at the proximal end of said lead, said socket having a first portion connected to the inner conductor of the lead and a second portion proximate the tip of said lead and adapted to receive a first electrical contact element connected to the circuits of said implantable medical device;

a conductive terminal mounted on the proximal end of said lead, said conductive terminal having an outer surface adapted to engage a second electrical contact element connected to the circuits of said implantable medical device and an inner surface couple to the outer conductor of said lead; and means mounted about the proximal end of the lead for sealingly engaging in fluid tight relationship said lead-receiving receptacle on said implantable medical device.

6. A lead, as defined in claim 5, in which the second portion of said socket includes yieldable electrical contact means adapted to provide a reliable electrical connection between said socket and said first electrical contact element connected to the circuit of said implantable medical device.

7. A lead, as defined in claim 6, in which said yieldable contact means comprises a coil garter spring contact.

8. A lead, as defined in claim 5, in which said sealingly engaging means includes a first elastomeric ring seal about the second portion of the socket and a second elastomeric ring seal, the conductive terminal being interposed between said first and said second ring seals.

9. A lead, as defined in claim 6, including:

an adapter terminal receivable by said second portion of the socket for connecting said lead for use with a standard VS-1 connector receptacle on said implantable medical device.

10. A connector assembly for an implantable medical device having electronic circuits, said connector assembly including:

(1) a receptacle comprising:
 (a) a side wall having an electrically conductive terminal for connection to the circuits of the implantable medical device;
 (b) an open end;
 (c) a closed end; and
 (d) an electrically conductive pin carried by said closed end, the pin having an inner portion disposed inside said receptacle and projecting toward the open end thereof, the pin including an end opposite the inner portion thereof for connection to the circuits of said implantable medical device; and (2) a bipolar lead for providing an electrically conductive path between the implantable medical device and a desired tissue location, the lead including:
 (a) a distal end for connection to the desired tissue location;
 (b) a proximal end adapted to be received by the open end of the receptacle;
 (c) a tip;
 (d) a pair of coaxial conductors including an inner conductor and an outer conductor, said conductors being insulated from each other;
 (e) a conductive socket mounted at the proximal end of said lead, said socket having a first portion connected to the inner conductor of the lead and a second portion proximate the tip of said lead for receiving the inner portion of the receptacle pin;
 (f) a conductive terminal mounted on the proximal end of said lead, said terminal having an outer surface for engaging the terminal on the side wall of the receptacle and an inner surface coupled to the outer conductor of said lead; and
 (g) means mounted about the proximal end of the lead for sealingly engaging in fluid light relationship the side wall of the receptacle.

11. A connector assembly, as defined in claim 10, in which the receptacle comprises an elongated tubular structure having a central longitudinal axis, said electrically conductive pin being centered on and extending along said longitudinal axis.

12. A connector assembly, as defined in claim 11, in which the terminal in the side wall of the receptacle comprises a conductive ring including yieldable contact means for engaging the conductive terminal on the proximal end of said lead.

13. A connector assembly, as defined in claim 12, in which said yieldable contact means comprises a coil garter spring contact.

14. A connector assembly, as defined in claim 10, in which the closed end of said receptacle comprises an electrically conductive end wall, the pin being integral with said end wall.

15. A connector assembly, as defined in claim 14, in which said receptacle includes an insulating tubular section interposed between the conductive ring and the conductive end wall.

16. A connector assembly, as defined in claim 10, in which the second portion of said socket includes yieldable electrical contact means adapted to provide a reliable electrical connection between said socket and said receptacle pin.

17. A connector assembly, as defined in claim 16, in which said yieldable contact means comprises a coil garter spring contact.

18. A connector assembly, as defined in claim 10, in which said sealingly engaging means includes a first elastomeric ring seal about the second portion of the socket and a second elastomeric ring seal, the conductive terminal on the proximal end of the lead being interposed between said first and said second ring seals.

* * * * *

UNITED STATES PATENT AND TRADEMARK OFFICE
CERTIFICATE OF CORRECTION

PATENT NO. : 5,324,311
DATED : June 28, 1994
INVENTOR(S) : Alfred D. Acken

It is certified that error appears in the above-indentified patent and that said Letters Patent is hereby corrected as shown below:

In col. 6, line 17, in Claim 9, delete "claim 6" and insert therefor --claim 5--.

Signed and Sealed this

Sixteenth Day of May, 1995

Attest:

BRUCE LEHMAN

Attesting Officer     *Commissioner of Patents and Trademarks*